United States Patent [19]

Angres

[11] 4,199,532

[45] Apr. 22, 1980

[54] METHOD FOR THE PRODUCTION OF HEXANITROSTILBENE

[75] Inventor: Isaac Angres, Gaithersburg, Md.

[73] Assignee: The United States of America as represented by the Secretary of the Navy, Washington, D.C.

[21] Appl. No.: 966,674

[22] Filed: Dec. 5, 1978

[51] Int. Cl.$^2$ ............................................. C07C 79/10
[52] U.S. Cl. ..................................................... 260/645
[58] Field of Search ......................................... 260/645

[56] References Cited

U.S. PATENT DOCUMENTS

| | | | |
|---|---|---|---|
| 3,267,159 | 8/1966 | Shipp | 260/646 |
| 3,505,413 | 4/1970 | Shipp | 260/645 |
| 3,992,432 | 11/1976 | Napier et al. | 260/465.1 |
| 4,085,152 | 4/1978 | Salter et al. | 260/645 |

OTHER PUBLICATIONS

Starks, J. Am. Chem. Soc., vol. 93, No. 1, pp. 195–199, (1971).
Dehmlow, Chemtech, Apr., 1975, pp. 210–218.

*Primary Examiner*—Leland A. Sebastian
*Attorney, Agent, or Firm*—R. S. Sciascia; A. L. Branning; R. D. Johnson

[57] ABSTRACT

A method of preparing 2,2',4,4',6,6'-hexanitrostilbene from 2,4,6-trinitrobenzyl chloride and hydroxyl ions using an organic solvent-water two phase system and a phase transfer catalyst.

10 Claims, No Drawings

METHOD FOR THE PRODUCTION OF HEXANITROSTILBENE

BACKGROUND OF THE INVENTION

This invention relates to explosives and more particularly to nitroaromatic explosives.

2,4,6-trinitrotoluene (TNT) shrinks when it cools, frequently causing TNT castings to crack. The addition of 1 percent by weight of 2,2',4,4',6,6'-hexanitrostilbene (HNS) to the TNT reduces or eliminates this shrinkage. HNS is also an excellent explosive. As a result, there is an increasing market for HNS.

Two methods of preparing 2,2',4,4',6,6'hexanitrostilbene (HNS) are disclosed in U.S. Pat. No. 3,505,413, entitled "Hexanitrostilbene," issued to Kathryn G. Shipp on Apr. 7, 1970. In the first 2,4,6-trinitrotoluene was reacted with 5 percent sodium hypochlorite (Clorox) at 0° C. in a tetrahydrofuran (THF)-methanol solvent mixture to produce HNS in a single step (disclosed yield 42%). In the second method, the above conditions were used except that the reaction was stopped after one minute by drowning the reaction mixture in very dilute hydrochloric acid. The reported yield of 2,4,6-trinitrobenzyl chloride was 85 percent. Next the 2,4,6-trinitrobenzyl chloride was reacted at room temperature with sodium hydroxide to give HNS (reported yield 50%). Thus, the yield of HNS using the two step method was $0.85 \times 0.50 = 0.425$ or 42.5%. It would be desirable to find a method of substantially increasing this yield.

SUMMARY OF THE INVENTION

Accordingly, an object of this invention is to provide a novel method of producing 2,2',4,4',6,6'-hexanitrostilbene.

Another object of this invention is to provide a method of producing 2,2',4,4',6,6'-hexanitrostilbene in increased yield.

These and other objects of the invention are accomplished by providing a method of preparing 2,2'4,4'6,6'-hexanitrostilbene from 2,4,6-trinitrobenzyl chloride comprising:
(1) contacting
  (a) an organic solvent phase comprising
    (i) 2,4,6-trinitrobenzyl chloride;
    (ii) a phase transfer catalyst of the formula

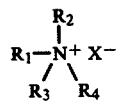

wherein $X^-$ is a halide ion, and $R_1$, $R_2$, $R_3$, and $R_4$ are monovalent hydrocarbon radicals having a total sum of from 12 to 70 carbon atoms; and
    (iii) an organic solvent selected from the group consisting of methylene chloride, chloroform, and 1,2-dichlorothane;
  with
  (b) an aqueous phase comprising
    (i) an alkali metal hydroxide; and
    (ii) water;
  and then
(2) isolating the product 2,2',4,4',6,6'-hexanitrostilbene.

DETAILED DESCRIPTION OF THE PREFERRED EMBODIMENT

The net reaction is

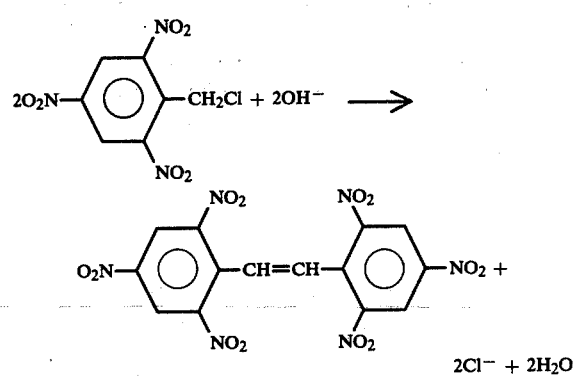

Thus, two moles of 2,4,6-trinitrobenzyl chloride and two moles of hydroxyl ion are consumed for each mole of 2,2',4,4',6,6'-hexanitrostilbene produced.

The 2,4,6-trinitrobenzyl chloride starting material can be produced by the method disclosed in U.S. Pat. No. 3,267,159, entitled "Preparation of 2,4,6-Trinitrobenzyl Halides," issued to Kathryn G. Shipp on Aug. 16, 1966.

An alkali metal hydroxide, preferably potassium hydroxide or sodium hydroxide, is used as the hydroxyl ion source; two moles of hydroxyl ions are required for the production of one mole of 2,2',4,4',6,6'-hexanitrostilbene.

The phase transfer catalyst can be represented by the formula

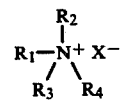

wherein $X^-$ is a halide ion, preferably chloride or bromide, and $R_1$, $R_2$, $R_3$ and $R_4$ are monovalent hydrocarbon radicals having a total sum of from 12 to 70 carbons atoms, and preferably from 15 to 50 carbon atoms. Monovalent hydrocarbons radicals here include alkyl, alkenyl, aryl, alkaryl, aralkyl, and cycloalkyl radicals. More preferred phase transfer catalysts are:

Triethylbenzyl ammonium chloride, didodecyldimethyl ammonium bromide, tetrabutyl ammonium chloride, and cetyltrimethyl ammonium chloride with triethylbenzyl ammonium chloride being the most preferred. The phase transfer catalyst is not consumed in the reaction; therefore, only a small amount, as little as one mole percent based on the number of moles of 2,4,6-trinitrobenzyl chloride, is required. A general discussion of Quaternary ammonium halide phase transfer catalysts is provided in U.S. Pat. No. 3,992,432, entitled "Phase Transfer Catalysis of Heterogeneous Reaction by Quaternary Salts," issued on Nov. 16, 1976, to Donald R. Napier and Charles M. Starks.

In the present process methylene chloride was found to work well as the solvent for the organic phase. Similar solvents, such as chloroform and 1,2-dichloroethane, should also be suitable. These organic solvents can be recovered by conventional means and reused.

The immiscible organic and water phases are preferably continuously mixed together (e.g., by stirring) to increase the surface area of contact between the two phases and thus speed up the reaction.

The general nature of the invention having been set forth, the following example is presented as a specific illustration thereof. It will be understood that the invention is not limited to this example but is susceptible to various modifications that will be recognized by one of ordinary skill in the art.

EXAMPLE

A solution of 2.6g (0.01 mole) of trinitrobenzyl chloride and 2.3g of triethylbenzyl ammonium chloride in 35 ml of methylene chloride was prepared in a small flask. To this solution there was added 0.01 mole of NaOH in 5 ml of water and the solution was stirred for 2 hours. The mixture was filtered and the filter cake of crude product was washed with methanol until the washings were colorless; then the crude product was dried in an oven at 100° C. It weighed 1.8g (75% of the theoretical). The m.p. of the crude material was 310°–312°.

Obviously, numerous modifications and variations of the present invention are possible in light of the above teaching. It is therefore to be understood that within the scope of the appended claims the invention may be practiced otherwise than as specifically described herein.

What is claimed as new and desired to be secured by Letters Patent of the U.S. is:

1. A method of preparing 2,2',4,4',6,6'-hexanitrostilbene from 2,4,6-trinitrobenzyl chloride comprising:
   (1) contacting
   (a) an organic solvent phase comprising
      (i) 2,4,6-trinitrobenzyl chloride;
      (ii) a phase transfer catalyst of the formula

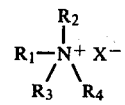

wherein $X^-$ is a halide ion, and $R_1$, $R_2$, $R_3$, and $R_4$ are monovalent hydrocarbon radicals having a total sum of from 12 to 70 carbon atoms; and
   (iii) an organic solvent selected from the group consisting of methylene chloride, chloroform, and 1,2-dichloroethane;
   with
   (b) an aqueous phase comprising
      (i) an alkali metal hydroxide;
      (ii) water;
   and then
   (2) isolating the product 2,2'4,4',6,6'-hexanitrostilbene.

2. The method of claim 1 wherein X is selected from the group consisting of bromide and chloride ions.

3. The method of claim 1 wherein the monovalent hydrocarbon radicals of the phase transfer catalyst have a total sum of from 15 to 50 carbon atoms.

4. The method of claim 3 wherein the phase transfer catalyst is selected from the group consisting of triethylbenezyl ammonium chloride, tetrabutyl ammonium chloride, didodecyldimethyl ammonium bromide, and cetyltrimethyl ammonium chloride.

5. The method of claim 4 wherein the phase transfer catalyst is triethylbenzyl ammonium chloride.

6. The method of claim 1 wherein the solvent is methylene chloride.

7. The method of claim 1 wherein the strong hydroxyl ion source is sodium hydroxide.

8. The method of claim 1 wherein the strong hydroxyl ion source is potassium hydroxide.

9. The method of claim 1 wherein the two phase mixture continuously mixed during step (1).

10. The method of claim 1 wherein the organic solvent is recovered by distilation.